(12) United States Patent
Mou et al.

(10) Patent No.: US 12,171,918 B2
(45) Date of Patent: Dec. 24, 2024

(54) BREAST PUMP

(71) Applicant: MICROJET TECHNOLOGY CO., LTD., Hsinchu (TW)

(72) Inventors: Hao-Jan Mou, Hsinchu (TW); Ching-Sung Lin, Hsinchu (TW); Yung-Lung Han, Hsinchu (TW); Chi-Feng Huang, Hsinchu (TW); Tsung-I Lin, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 368 days.

(21) Appl. No.: 17/577,438

(22) Filed: Jan. 18, 2022

(65) Prior Publication Data
US 2023/0211054 A1 Jul. 6, 2023

(30) Foreign Application Priority Data
Jan. 4, 2022 (TW) .................................. 111100205

(51) Int. Cl.
*A61M 1/06* (2006.01)
*A61M 39/24* (2006.01)

(52) U.S. Cl.
CPC ............ *A61M 1/066* (2014.02); *A61M 39/24* (2013.01); *A61M 1/067* (2021.05); *A61M 2205/07* (2013.01); *A61M 2205/581* (2013.01)

(58) Field of Classification Search
CPC ......................... A61M 1/06935; A61M 1/0697
See application file for complete search history.

(56) References Cited

U.S. PATENT DOCUMENTS

| 9,480,783 | B2 | 11/2016 | Johnson et al. | |
| 2002/0198489 | A1* | 12/2002 | Silver | A61M 1/064 119/14.47 |
| 2006/0270973 | A1* | 11/2006 | Chu | A61M 1/067 604/74 |
| 2008/0208116 | A1* | 8/2008 | Dao | A61M 1/064 604/74 |

(Continued)

FOREIGN PATENT DOCUMENTS

| CN | 110662482 A | 1/2020 |
| CN | 111001054 A | 4/2020 |

(Continued)

*Primary Examiner* — Courtney B Fredrickson
(74) *Attorney, Agent, or Firm* — Birch, Stewart, Kolasch & Birch, LLP

(57) ABSTRACT

A breast pump includes a main body, a breast milk suctioning shield, and one or more air pumps. The breast milk suctioning shield is assembled in an accommodation space of the main body and detachably connected to the main body. A front end of the breast milk suctioning shield has a breast shielding portion, and a nipple passage extends from a rear end of a center portion of the breast shielding portion. One or more deformable members and a non-deformable supporting member are assembled with an annular connection portion located between the breast shielding portion and the nipple passage. The air pump has an intake port and an exhaust port. The intake port is controlled by a first valve controller to suction the nipple passage and generate a negative pressure, and the exhaust port is controlled by a second valve controller to inflate or deflate the deformable member.

18 Claims, 7 Drawing Sheets

(56) References Cited

U.S. PATENT DOCUMENTS

| | | | | |
|---|---|---|---|---|
| 2010/0094078 A1* | 4/2010 | Weston | ............... | A61M 1/0693 |
| | | | | 604/74 |
| 2015/0065994 A1* | 3/2015 | Fridman | ............ | A61M 1/0697 |
| | | | | 604/74 |
| 2016/0220743 A1* | 8/2016 | Guthrie | ................. | G06F 3/0482 |
| 2017/0112983 A1* | 4/2017 | Thorne | ................ | A61M 1/067 |
| 2018/0001001 A1 | 1/2018 | Wu et al. | | |
| 2018/0126052 A1* | 5/2018 | Looney | ................... | A61M 1/06 |
| 2018/0361040 A1* | 12/2018 | O'Toole | ............. | A61M 1/0697 |
| 2020/0078503 A1* | 3/2020 | Bartlett | ................. | A61M 1/062 |
| 2021/0069391 A1* | 3/2021 | Quackenbush | ....... | A61M 1/064 |
| 2021/0205513 A1 | 7/2021 | O'Toole et al. | | |

FOREIGN PATENT DOCUMENTS

| | | | |
|---|---|---|---|
| CN | 111655305 A | 9/2020 | |
| JP | 2017527337 A | 9/2017 | |
| JP | 2020523128 A | 8/2020 | |
| JP | 2020523179 A | 8/2020 | |
| TW | 200618826 A | 6/2006 | |

\* cited by examiner

BREAST PUMP

CROSS-REFERENCE TO RELATED APPLICATION

This non-provisional application claims priority under 35 U.S.C. § 119(a) to patent application Ser. No. 11/100,205 in Taiwan, R.O.C. on Jan. 4, 2022, the entire contents of which are hereby incorporated by reference.

BACKGROUND

Technical Field

The present disclosure relates to a breast milk collecting device which is suitable for breast-feeding and is hands-free, in particular, to a breast pump suitable for wearing.

Related Art

Passive breast milk collection is an area of breastfeeding that is worth to be addressed. Passive breast milk release is originated from the natural "breast milk releasing" phenomenon occurring to a woman upon an infant "sucks" the breast of the woman for breast-feeding. When the breast is stimulated to release the breast milk by applying a suctioning force to the breast, owing to this "lactation phenomenon", before collecting, a plenty of breast milk that can be collected into the feeding bottles to feed the infants is wasted by most mothers who adopt breast-feeding. Therefore, a novel breast milk collecting device is required to collect the breast milk passively released from the breast for subsequent feeding. Hence, a breast milk collecting device which is hands-free, hiddenable, and ergonomic is provided in this invention, the breast milk collecting device is a breast pump that does not need to be operated manually and is easy to be placed, disassembled, cleaned, and reassembled. Moreover, the user can place the breast pump under the daily cloth without taking off cloth or wearing complicated and apparent holding straps to execute a hands-free breast milk collection procedure.

Furthermore, it is understood that, the commercial breast pump merely performs a breast milk suctioning operation through continuously applying a negative-pressure on the breast, and thus is devoid of an operation mode corresponding to the "lactation phenomenon" of a woman's breast. As a result, the conventional breast pump can just suction the breast milk currently secreted by the breast, and no further breast milk can be suctioned from the breast by the conventional breast pump after the conventional breast pump performs the breast milk suctioning operation to a woman's breast for a while. Thereafter, the woman conducting breast-feeding will feel pain and uncomfortable at her breast as the breast pump continuously suctions her breast. Hence, the conventional breast pump fails to mimic the natural "lactation phenomenon" occurred when an infant "sucks" the breast of the woman and allow the pituitary gland of the woman to be stimulated to secret prolatine or oxytocin to allow the mammary gland of the breast to produce the breast milk. Consequently, how to provide a breast pump capable of performing intermittent and automatic suctioning operation to mimic the natural "lactation phenomenon" is an issue of concern to be developed in this invention.

SUMMARY

One object of the present disclosure is to provide a breast pump, wherein a negative-pressure breast milk suctioning operation can be achieved by controlling the air intake and air exhaustion of the air pump through a first valve controller and a second valve controller. Furthermore, the deformable member can also be inflated and deflated alternately to touch and press the breast to mimic infants' suckling behaviors, so as to allow the pituitary gland of the user to be stimulated to secret prolatine or oxytocin and allow the mammary gland of the breast to produce the breast milk during the breast milk suctioning operation. Moreover, a first detector and/or a second detector of the breast pump are provided to determine whether the breast milk is released from the mammary gland of the breast, so as to control the operation of the air pump. The exhaust port of the air pump is controlled by the second valve controller to inflate or deflate the deformable member alternately to touch and press the breast to mimic infants' suckling behaviors. Furthermore, the first detector and/or the second detector, along with the first valve controller and the second valve controller, controls the air intake and exhaustion of the air pump so as to allow the breast pump to adjust the suctioning force and control the operation frequency of the air pump. Therefore, the breast pump of one or some embodiments of the invention can provide a proper breast milk suctioning operation which can be performed automatically and intermittently to mimic infants' suckling behaviors without leading to any pain or uncomfortable.

To achieve the object mentioned above, in one embodiment of the present disclosure, a breast pump is provided to be placed at a breast of a user for collecting breast milk. The breast pump includes a main body, a breast milk suctioning shield, and at least one air pump. The main body has an accommodation space. The breast milk suctioning shield is assembled in the accommodation space and detachably connected to the main body. A front end of the breast milk suctioning shield has a breast shielding portion, and a nipple passage extends from a rear end of a center portion of the breast shielding portion. At least one deformable member is assembled with an annular connection portion between the breast shielding portion and the nipple passage. The at least one air pump has an intake port and an exhaust port. The intake port is controlled by a first valve controller to suction the nipple passage and generate a negative pressure, and the exhaust port is controlled by a second valve controller to inflate or deflate the at least one deformable member.

BRIEF DESCRIPTION OF THE DRAWINGS

The disclosure will become more fully understood from the detailed description given herein below, for illustration only and thus not limitative of the disclosure, wherein.

DETAILED DESCRIPTION

Figure 1:
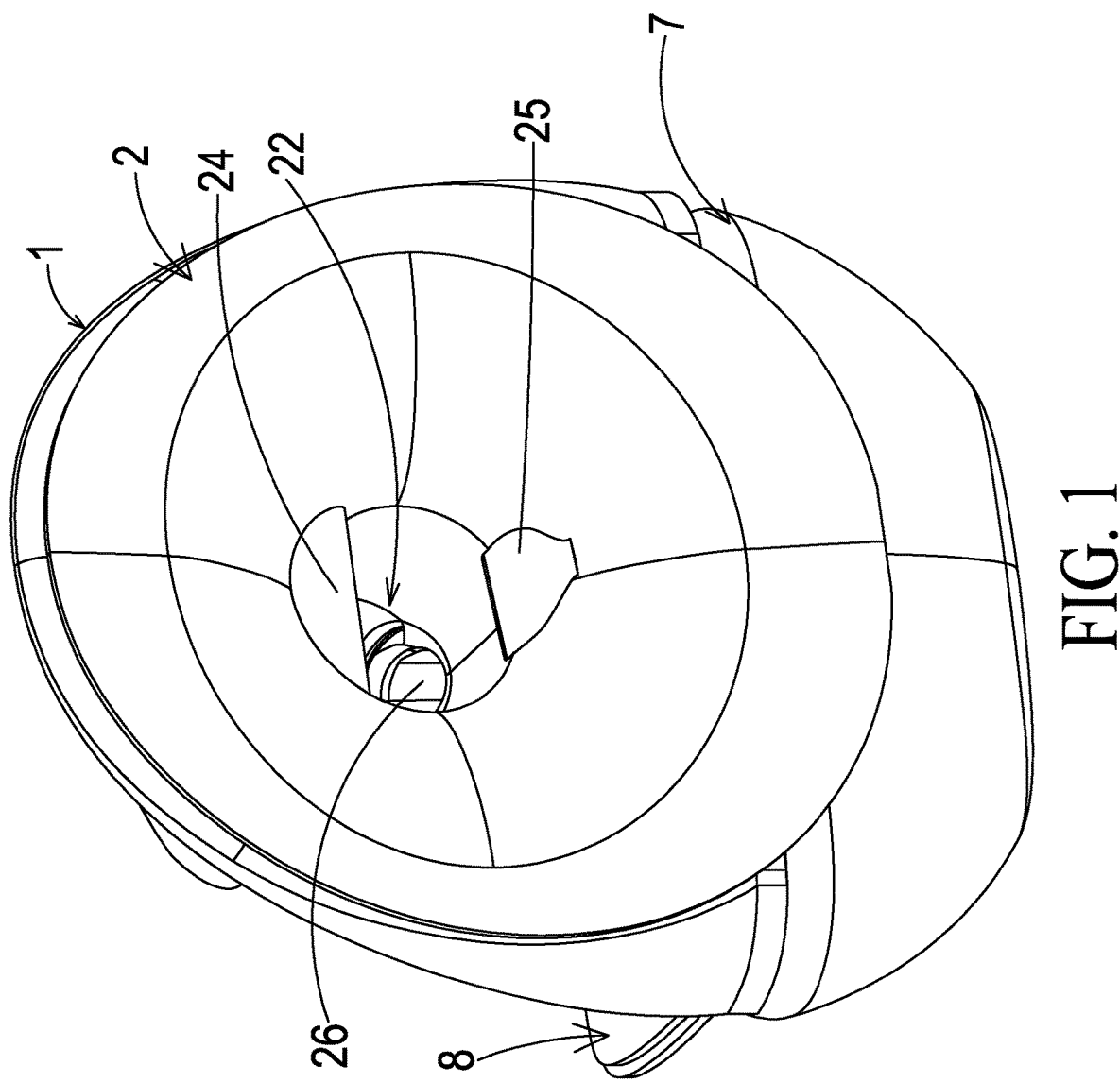
FIG. 1 illustrates a schematic perspective view of a breast pump according to an exemplary embodiment of the present disclosure.

The present disclosure will now be described more specifically with reference to the following embodiments. It is to be noted that the following descriptions of different embodiments of this disclosure are presented herein for purpose of illustration and description only, and it is not intended to limit the scope of the present disclosure.

Please refer to FIG. 1 to FIG. 7. In one embodiment, a breast pump is provided and includes a main body 1, a breast milk suctioning shield 2, a first valve controller 3, at least one air pump 4, a second valve controller 5, a duckbill valve 6, a breast milk container 7, a connector component 8, and a flexible separation film 9.

Figure 7:
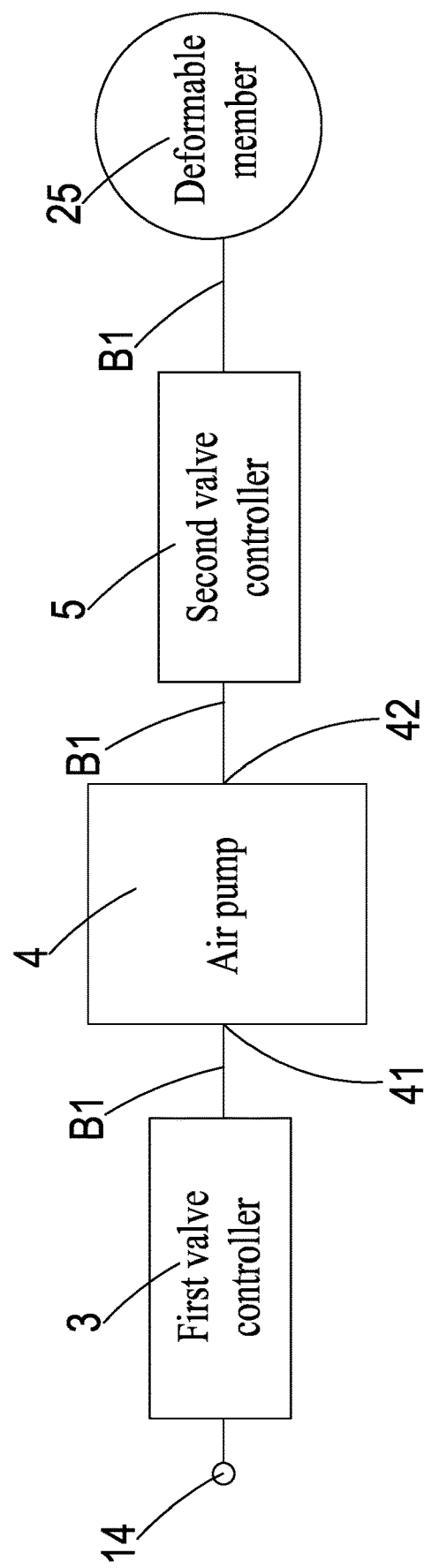
FIG. 7 illustrates a schematic diagram showing the breast milk suctioning operation of the air pump of the breast pump of the exemplary embodiment of the present disclosure.

As shown in FIG. 2, FIG. 3, FIG. 4, and FIG. 7, the main body 1 has a accommodation space 11, and the accommodation space 11 includes an opening 12 and a separation film recess 13. The separation film recess 13 is in communication with an air port 14, and the air port 14 is connected to the first valve controller 3 outside the main body 1 through a pipeline B1 (as shown in FIG. 7).

Figure 2:
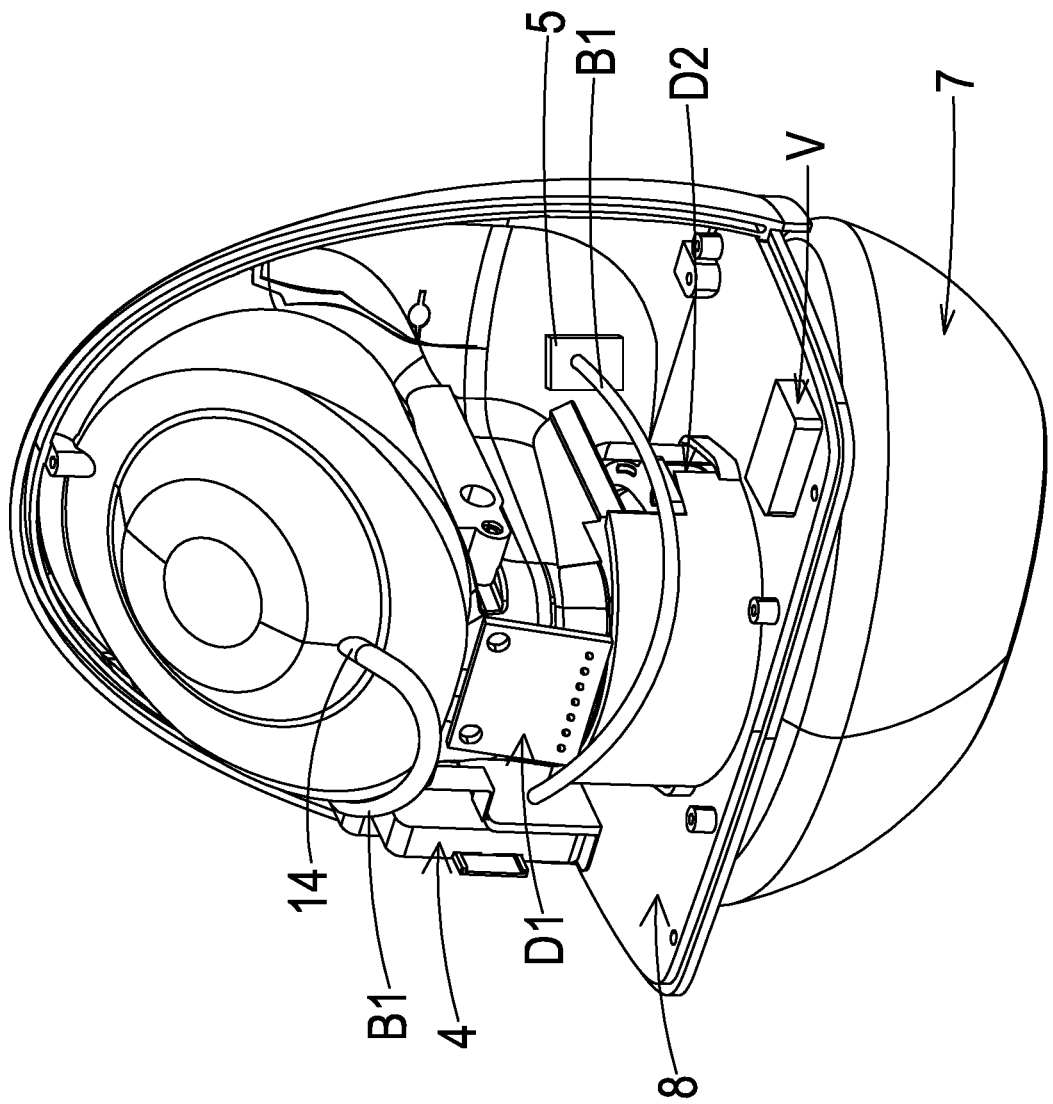
FIG. 2 illustrates a schematic perspective view of the breast pump of the exemplary embodiment of the present disclosure from another view angle.
Figure 3:
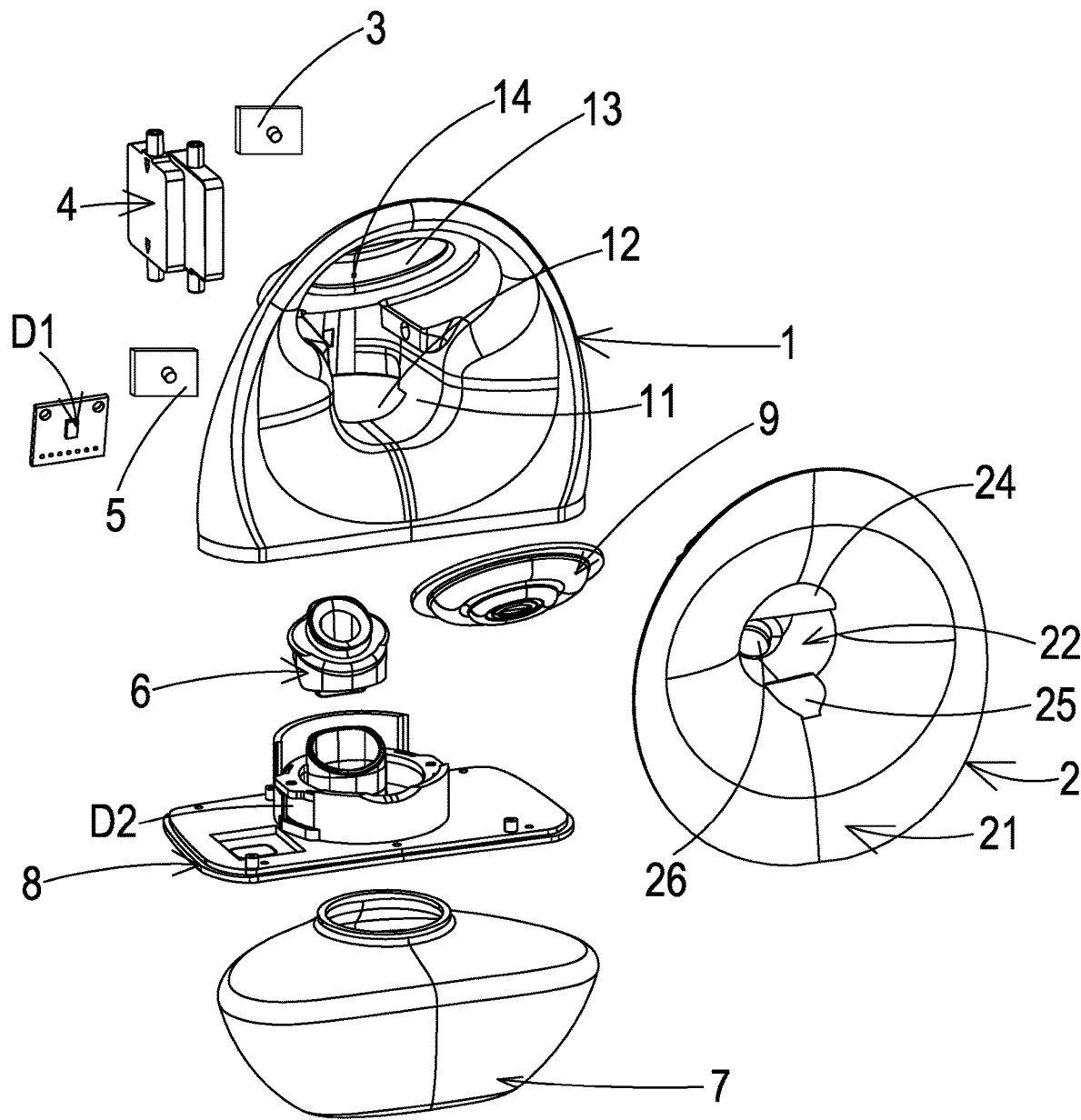
FIG. 3 illustrates an exploded view of the breast pump of another exemplary embodiment of the present disclosure.
Figure 4:
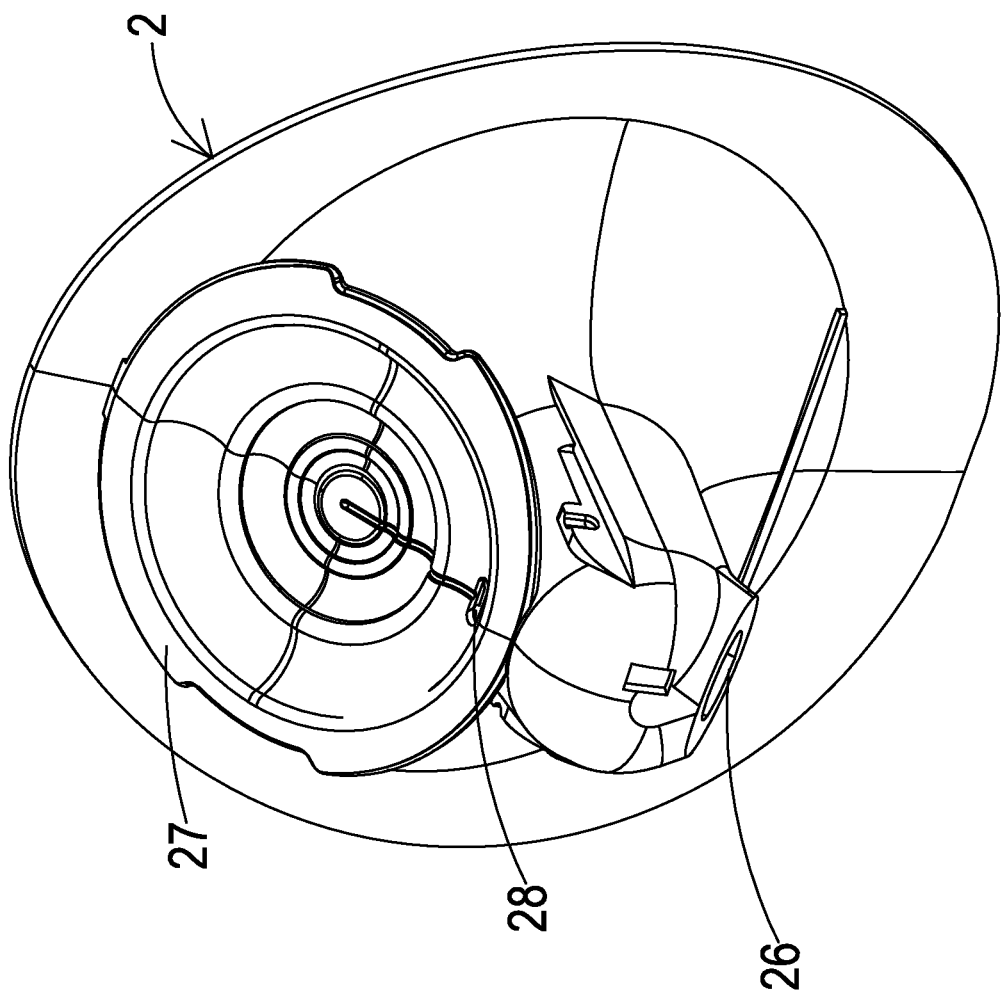
FIG. 4 illustrates a schematic view of a breast milk suctioning shield of the breast pump of the exemplary embodiment of the present disclosure.

Furthermore, as shown in FIG. 2, FIG. 3, and FIG. 4, the breast milk suctioning shield 2 is transparent and is made of a rigid material or a semi-rigid material, the breast milk suctioning shield 2 is assembled in the accommodation space 11 of the main body 1, and the breast milk suctioning shield 2 is detachably connected to the main body 1. A front end of the breast milk suctioning shield 2 has a breast shielding portion 21, and a nipple passage 22 extends from a rear end of a center portion of the breast shielding portion 21. At least one deformable member 25 is assembled with an annular connection portion 23 located between the breast shielding portion 21 and the nipple passage 22. In one embodiment, the breast milk suctioning shield 2 further includes a non-deformable supporting member 24 placed at a location corresponding to the at least one deformable member 25 in the annular connection portion 23. In one embodiment, one deformable member 25 and one non-deformable supporting member 24 opposite to the deformable member 25 are assembled in the annular connection portion 23 between the breast shielding portion 21 and the nipple passage 22, but not limited thereto. The number of the deformable member 25 and the non-deformable supporting member 24 can be adjusted according to actual requirements. In one embodiment, the breast shield portion 21 is made of a flexible material and is adapted to be closely attached to the breast of the user, but not limited thereto. In one embodiment, the non-deformable supporting member 24 is made of a semi-rigid material and may be a flange structure, but not limited thereto. In one embodiment, the deformable member 25 is made of a flexible material which is capable of being inflated and expanded or deflated and contracted. Alternatively, in one embodiment, the deformable member 25 may be made of silicone rubber or thermoplastic polyurethane (TPU). In one embodiment, the deformable member 25 is an air bag and is capable of being inflated and expanded or deflated and contracted, but not limited thereto.

Further, as shown in FIG. 3 and FIG. 4, the nipple passage 22 of the breast milk suctioning shield 2 has a breast milk outlet 26 corresponding to the opening 12 of the main body 1. Moreover, the breast milk container 7 is assembled at a bottom portion of the main body 1, and a connector component 8 is disposed between the bottom portion of the main body 1 and the breast milk container 7, so that the breast milk container 7 is corresponding to the connector component 8 and can be assembled to the bottom portion of the main body 1 through the connector component 8, and the breast milk container 7 is corresponding to the breast milk outlet 26 of the nipple passage 22 to form an outflow passage H.

Figure 5:
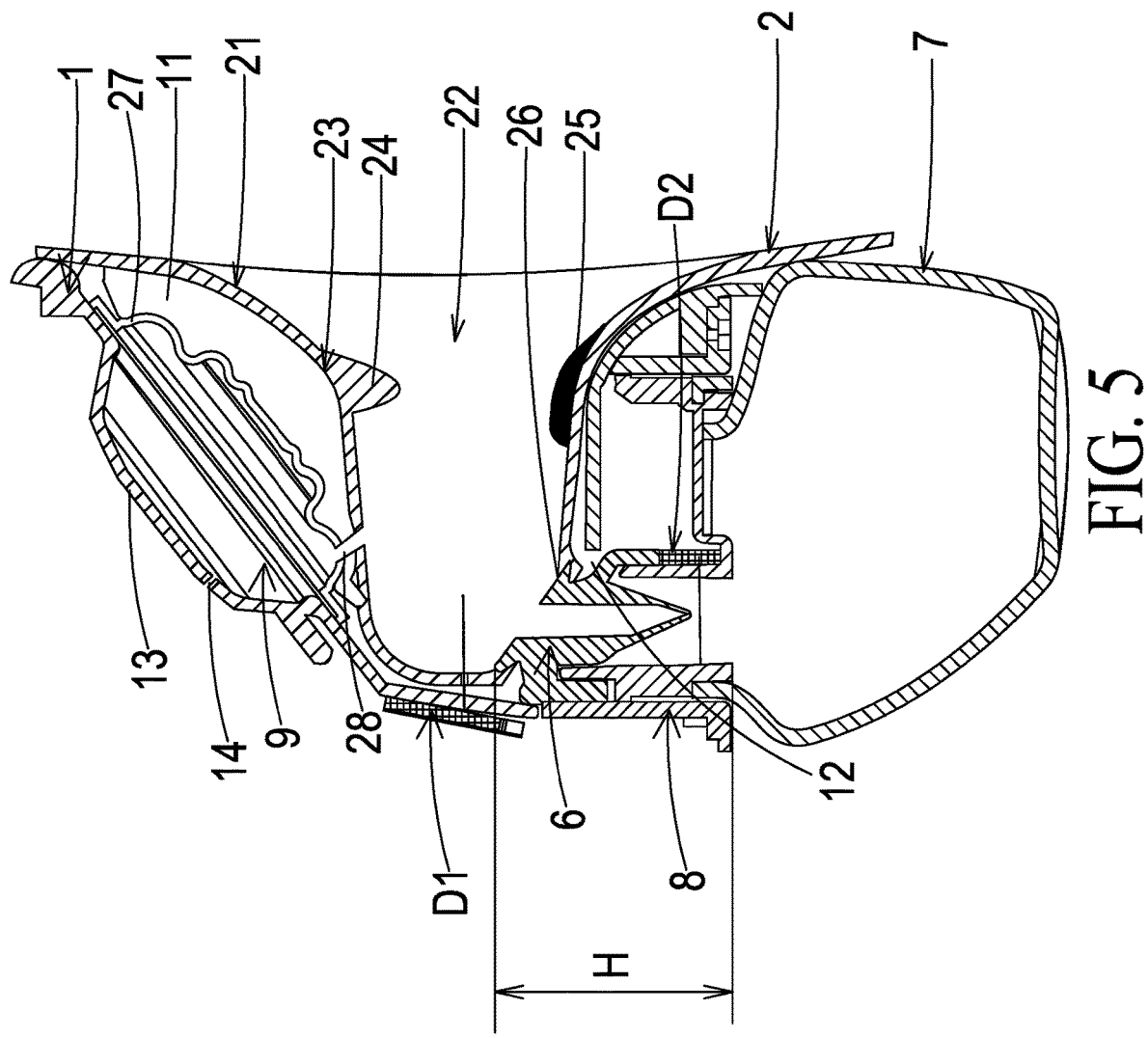
FIG. 5 illustrates a cross-sectional view of the breast pump of the exemplary embodiment of the present disclosure.
Figure 6:
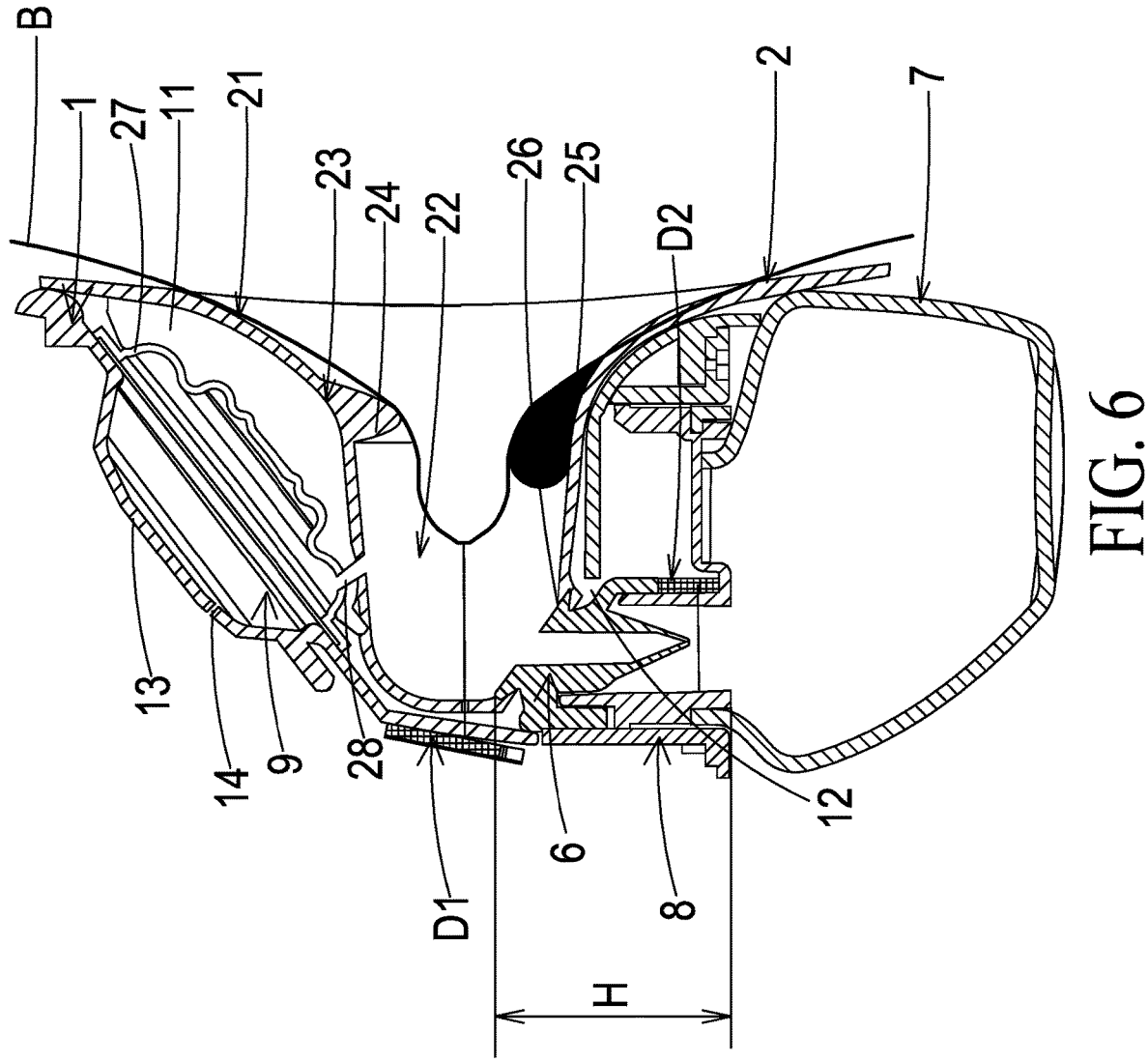
FIG. 6 illustrates a cross-sectional view showing the breast milk suctioning operation of the breast pump of the exemplary embodiment of the present disclosure.

As shown in FIG. 4 and FIG. 5, the duckbill valve 6 is disposed at the breast milk outlet 26 of the nipple passage 22. When the breast milk is inside the nipple passage 22, the breast milk flows into the duckbill valve 6 through the breast milk outlet 26, so that the duckbill valve 6 is automatically opened to allow the breast milk to flow into the outflow passage H smoothly to be collected in the breast milk container 7. On the other hand, when no breast milk flows into the duckbill valve 6, the duckbill valve 6 is closed to prevent the breast milk in the breast milk container 7 from flowing back to the breast milk outlet 26 of the nipple passage 22. Moreover, a separation film base 27 is assembled on an outer portion of the breast shielding portion 21 of the breast milk suctioning shield 2, and the separation film base 27 has a negative-pressure port 28 in communication with the nipple passage 22. The flexible separation film 9 is assembled and positioned in the separation film base 27, and the breast milk suctioning shield 2 is assembled in the accommodation space 11 of the main body 1. The separation film base 27 is connected to the separation film recess 13, so that the flexible separation film 9 is completely sealed and positioned between the separation film base 27 and the separation film recess 13. Furthermore, the air port 14 of the separation film recess 13 is connected to the first valve controller 3 outside the main body 1 through the pipeline B1.

Moreover, as shown in FIG. 7, the air pump 4 has an intake port 41 and an exhaust port 42. The intake port 41 is connected to the first valve controller 3 through the pipeline B1, the exhaust port 42 is connected to the second valve controller 5 through the pipeline B1, and the second valve controller 5 is connected to the deformable member 25 through the pipeline B1. In one embodiment, the breast pump includes a plurality of the air pumps 4, and the air pumps 4 are assembled in the pipeline B1 in a series-connection manner or a parallel-connection manner, but not limited thereto. In one embodiment, the air pump 4 is a piezoelectric pump; alternatively, in another embodiment, the air pump 4 is an electric pump that may be a motor, a pneumatic pump, an electromagnetic pump, or other power-driven pumping device, but not limited thereto. Moreover, the first valve controller 3 may be an electromagnetic valve and the second valve controller 5 may be an electromagnetic valve, but not limited thereto.

As mentioned above, as shown in FIG. 6 and FIG. 7, the breast shielding portion 21 of the breast milk suctioning shield 2 is adapted to be placed at the breast B of the user with the nipple of the breast B being placed in the nipple passage 22. When the air pump 4 is enabled, the intake port 41 of the air pump 4 is controlled by the first valve controller 3 to suction and a negative-pressure suctioning force is generated and transmitted to the separation film recess 13, so that the flexible separation film 9 between the separation film base 27 and the separation film recess 13 is deformed and generates the negative-pressure suctioning force in the separation film base 27 which results in the negative-pressure suctioning force in the nipple passage 22 through the negative-pressure port 28. Hence, a breast milk suctioning operation of the breast pump is applied to the breast B.

Moreover, when the air pump 4 is enabled, the exhaust port 42 of the air pump 4 is controlled by the second valve controller 5 to exhaust a gas or not to exhaust the gas. Hence, the deformable member 25 is inflated by the gas, on the contrary, e the gas does not enter into the deformable member 25 and thus the deformable member 25 is deflated. Therefore, the deformable member 25 is inflated and deflated alternately to touch and press the breast B. Hence, the breast pump can mimic the sucking or touching behaviors of an infant (also including licking and sucking) to the breast B. Alternatively, in one embodiment, the exhaust port 42 of the air pump 4 is controlled by the second valve controller 5 to output a gas or not to output the gas. Hence, the deformable member 25 is inflated and deflated alternately to press and touch the breast B, and the breast B is further touched, pressed, and held together by the non-deformable supporting member 24 and the deformable member 25. Hence, the breast pump can properly mimic the "sucking" or "licking" behaviors of an infant to the breast B, so as to reproduce the lactation phenomenon occurs in the user and stimulate the pituitary gland of the user to secret prolatine or oxytocin and allow the mammary gland of the breast B to produce the breast milk.

Moreover, in one embodiment, a first detector D1 is disposed at a rear portion of the nipple passage 22 of the breast milk suctioning shield 2, the first detector D1 detects whether the breast B ejects the breast milk and determines whether the breast milk is released from the mammary gland of the breast B by detecting breast milk inside the nipple passage. In another embodiment, a second detector D2 is disposed on the periphery of the outflow passage H, and the second detector D2 detects whether the breast B ejects the breast milk and determines whether the breast milk is released from the mammary gland of the breast B by detecting breast milk flowing through the outflow passage.

When the first detector D1 or the second detector D2 detects and determines that the breast milk is not released from the mammary gland of the breast B by detecting none of the breast milk inside the nipple passage or none of the breast milk flowing through the outflow passage, respectively, the first detector D1 or the second detector D2 enables the air pump 4 to inflate and deflate the deformable member 25 alternately through the second valve controller 5 to press and touch the breast B. Hence, the breast pump can mimic the "licking" and "sucking" behaviors of an infant to the breast B. Consequently, the breast B is stimulated to eject the breast milk. In another embodiment, the first detector D1 or the second detector D2 enables the air pump 4 to inflate and deflate the deformable member 25 alternately through the second valve controller 5 to press and touch the breast B, and the breast B is further touched, pressed, and held together by the non-deformable supporting member 24 and the deformable member 25 to properly mimic the "licking" and "sucking" behaviors of an infant to the breast B. Consequently, the breast B is stimulated to eject the breast milk.

As mentioned, according to one or some embodiments of the present disclosure, the breast pump provides an intermittent and automatic operation for suctioning the breast milk. The first detector D1 and/or the second detector D2 of the breast pump are provided to determine whether the breast milk is released from the mammary gland of the breast B and control the operation of the air pump 4. The exhaust port 42 of the air pump 4 can be controlled by the second valve controller 5 to inflate or deflate the deformable member 25 alternately to touch and press the breast B to mimic infants' suckling behaviors so as to allow the pituitary gland of the user to be stimulated to secret prolatine or oxytocin and allow the mammary gland of the breast B to produce the breast milk during the breast milk suctioning operation. Furthermore, the first detector D1 and/or the second detector D2, along with the first valve controller 3 and the second valve controller 5 control the air intake and exhaustion of the air pump 4 so as to allow the breast pump to adjust the suctioning force and control the operation frequency of the air pump 4, thereby achieving an intermittent and automatic operation for suctioning the breast milk. In other words, in this embodiment, when the first detector D1 and/or the second detector D2 detects that the breast milk is not released from the mammary gland of the breast B, the intake port 41 of the air pump 4 is controlled by the first valve controller 3 to stop the generation of the negative-pressure suctioning force so as to stop the deformation of the flexible separation film 9, and thus the negative-pressure suctioning force is not generated in the nipple passage 22. Hence, the continuously suctioning operation is not continued when the breast milk is not released without leading to any pain or uncomfortable of the user. Moreover, the exhaust port 42 of the air pump 4 is controlled by the second valve controller 5 to exhaust a gas or not to exhaust the gas. Hence, the deformable member 25 of the breast pump of one or some embodiments of the present invention can be inflated and deflated alternately to press and touch the breast B so as to mimic infants' suckling behaviors. Furthermore, the infants' suckling behaviors can also be mimicked through pressing and holding the breast B of the user by the deformable member 25 against the non-deformable supporting member 24. Therefore, during the breast milk suctioning operation, the pituitary gland of the user is stimulated to secret prolatine or oxytocin and allow the mammary gland of the breast B to produce the breast milk. Moreover, in some embodiments, the first detector D1 and/or the second detector D2 of the breast pump is provided to determine whether the breast milk is released from the mammary gland of the breast B. Moreover, the first detector D1 or the second detector D2, along with the first valve controller 3 and the second valve controller 5, controls the air intake and exhaustion of the air pump 4 so as to allow the breast pump to adjust the suctioning force and control the operation frequency of the air pump. Therefore, the breast pump of one or some embodiments of the invention can provide a proper breast milk suctioning operation which can be performed automatically and intermittently to mimic infants' suckling behaviors without leading to any pain or uncomfortable of the user.

It is understood that the infant's sound or suckling sound can stimulate the pituitary gland of the user to secret prolatine or oxytocin so as to induce the "lactation phenomenon".

Hence, in one embodiment, the breast pump further includes a sound recording device, or sound recorder, V, and the sound recording device V can record sounds of infant (e.g., the sounds of crying, laughing, or sucking). The sound of the user's infant can be recorded by the sound recording device during breast feeding, and the sound recording device can replay the infant sound when the user uses the breast pump. Hence, in this embodiment, in addition to the intermittent and automatic operation for suctioning the breast milk, the user can also hear the infant sound to stimulate the pituitary gland of the user to secret prolatine or oxytocin and allow the mammary gland to produce the breast milk.

As mentioned above, according to one or some embodiments of the present disclosure, the present invention provides a breast pump, wherein the air intake and air exhaustion of the air pump is controlled by the first valve controller and the second valve controller, so as to achieve a negative-pressure breast milk suctioning operation. Further, the deformable member is inflated and deflated alternately to touch and press the breast to mimic infants' suckling behaviors so as to allow the pituitary gland of the user to be stimulated to secret prolatine or oxytocin and allow the mammary gland of the breast to produce the breast milk during the breast milk suctioning operation. Moreover, the first detector and/or the second detector of the breast pump are provided to determine whether the breast milk is released from the mammary gland of the breast, so that the operation of the air pump is controlled accordingly, and the exhaust port of the air pump is controlled by the second valve controller to inflate or deflate the deformable member alternately to touch and press the breast to mimic infants' suckling behaviors. Furthermore, the first detector and/or the second detector, along with the first valve controller and the second valve controller control the air intake and exhaustion of the air pump so as to allow the breast pump to adjust the suctioning force and control the operation frequency of the air pump accordingly. Therefore, the breast pump of one or some embodiments of the invention can provide a proper breast milk suctioning operation which can be performed automatically and intermittently to mimic infants' suckling behaviors without leading to any pain or uncomfortable of the user.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A breast pump adapted to be placed at a breast of a user to collect breast milk, wherein the breast pump comprises:
    a main body having an accommodation space;
    a breast milk suctioning shield assembled in the accommodation space and detachably connected to the main body, wherein a front end of the breast milk suctioning shield has a breast shielding portion, and a nipple passage extends from a rear end of a center portion of the breast shielding portion; at least one deformable member is assembled with an annular connection portion located between the breast shielding portion and the nipple passage;
    at least one air pump, wherein the at least one air pump has an intake port and an exhaust port; the intake port is controlled by a first valve controller to suction the nipple passage and generate a negative pressure, and the exhaust port is controlled by a second valve controller to inflate or deflate the at least one deformable member;
    a flexible separation film; and
    a separation film base,
    wherein the main body is sequentially connected to the first valve controller, the at least one air pump, the second valve controller, and the at least one deformable member outside the main body through a pipeline; when the at least one air pump is enabled, the intake port of the at least one air pump is controlled by the first valve controller to suction the nipple passage and generate the negative pressure, and the exhaust port of the at least one air pump is controlled by the second valve controller to inflate or deflate the at least one deformable member;
    wherein the accommodation space of the main body comprises a separation film recess in communication with an air port, and the air port is connected to the first valve controller outside the main body through the pipeline; the separation film base is assembled on an outer portion of the breast shielding portion of the breast milk suctioning shield, and the separation film base has a negative-pressure port in communication with the nipple passage; the flexible separation film is assembled and positioned in the separation film base, and the breast milk suctioning shield is assembled in the accommodation space of the main body; the separation film base is connected to the separation film recess, so that the flexible separation film is completely sealed and positioned between the separation film base and the separation film recess; when the at least one air pump is enabled, the intake port of the at least one air pump is controlled by the first valve controller to suction and generate a negative-pressure suctioning force, the flexible separation film is deformed between the separation film base and the separation film recess and generates the negative-pressure suctioning force in the separation film base which results in the negative-pressure suctioning force in the nipple passage through the negative-pressure port, so that a breast milk suctioning operation of the breast pump can be achieved.

2. The breast pump according to claim 1, wherein the at least one air pump is a piezoelectric pump, an electric pump, or a combination thereof.

3. The breast pump according to claim 1, wherein the at least one air pump comprises a plurality of air pumps, and the air pumps are assembled in the breast pump in a series-connection manner, a parallel-connection manner, or a combination thereof.

4. The breast pump according to claim 1, wherein the first valve controller or the second valve controller is an electromagnetic valve.

5. The breast pump according to claim 1, wherein the at least one deformable member is made of a flexible material.

6. The breast pump according to claim 1, wherein the at least one deformable member is made of silicone rubber or thermoplastic polyurethane (TPU).

7. The breast pump according to claim 1, wherein the at least one deformable member is an airbag.

8. The breast pump according to claim 1, wherein the breast milk suctioning shield further comprises a non-deformable supporting member placed at a location corresponding to the at least one deformable member in the annular connection portion.

9. The breast pump according to claim 8, wherein the non-deformable supporting member is a flange structure.

10. The breast pump according to claim 1, wherein the breast milk suctioning shield is transparent and made of a rigid material or a semi-rigid material, and the breast shielding portion of the breast milk suctioning shield is made of a flexible material.

11. The breast pump according to claim 8, the breast shielding portion of the breast milk suctioning shield is adapted to be placed at the breast of the user, and the nipple passage is adapted to receive a nipple of the breast; the second valve controller controls the at least one air pump to inflate and deflate the at least one deformable member alternately to press and touch the breast, and the breast is further touched, pressed, and held together by the non-deformable supporting member and the at least one deformable member, so as to allow the mammary gland of the breast to be stimulated to eject the breast milk.

12. The breast pump according to claim 1, wherein a first detector is disposed at a rear portion of the nipple passage of the breast milk suctioning shield to detect the breast milk inside the nipple passage; when the first detector detects none of the breast milk inside the nipple passage, the first detector enables the at least one air pump to inflate and deflate the at least one deformable member alternately through the second valve controller.

13. The breast pump according to claim 12, wherein the breast milk suctioning shield further comprises a non-deformable supporting member placed at a location corresponding to the at least one deformable member in the annular connection portion.

14. The breast pump according to claim 1, wherein the accommodation space of the main body has an opening, and the nipple passage of the breast milk suctioning shield has a breast milk outlet corresponding to the opening; a bottom portion of the main body is assembled with a breast milk container, and a connector component is disposed between the main body and the breast milk container, so that the breast milk container is corresponding to the connector component and is assembled to the bottom portion of the main body through the connector component, and the breast milk container is corresponding to the breast milk outlet of the nipple passage to form an outflow passage.

15. The breast pump according to claim 14, wherein a duckbill valve is further disposed at the breast milk outlet of the nipple passage; when the breast milk flows into the nipple passage, the breast milk flows into the duckbill valve through the breast milk outlet, so that the duckbill valve is automatically opened to allow the breast milk to flow into the outflow passage smoothly to be collected in the breast milk container; when no breast milk flows into the duckbill valve, the duckbill valve is closed to prevent the breast milk in the breast milk container from flowing back to the breast milk outlet of the nipple passage.

16. The breast pump according to claim 14, wherein a second detector is disposed on the periphery of the outflow passage to detect the breast milk flowing through the outflow passage; when the second detector detects none of the breast milk flowing through the outflow passage, the second detector enables the at least one air pump to inflate and deflate the at least one deformable member alternately through the second valve controller.

17. The breast pump according to claim 16, wherein the breast milk suctioning shield further comprises a non-deformable supporting member placed at a location corresponding to the at least one deformable member in the annular connection portion.

18. The breast pump according to claim 1, further comprising a sound recorder adapted to record an infant sound and replay the infant sound.

\* \* \* \* \*